United States Patent
Martin et al.

(10) Patent No.: US 11,203,575 B2
(45) Date of Patent: Dec. 21, 2021

(54) METHHOD FOR PRODUCING A CRYSTALLINE FORM OF 5-AMINO-2,3-DIHYDROPHTHALAZINE-1,4-DIONE

(71) Applicant: METRIOPHARM AG, Zürich (CH)

(72) Inventors: Thomas Martin, Selb (DE); Josef Breu, Bayreuth (DE); Juliane Fleissner, Hof (DE); Wolfgang Brysch, Berlin (DE); Jörg Von Wegerer, Berlin (DE)

(73) Assignee: MetrioPharm AG, Zürich (CH)

( * ) Notice: Subject to any disclaimer, the term of this patent is extended or adjusted under 35 U.S.C. 154(b) by 393 days.

(21) Appl. No.: 15/999,050

(22) PCT Filed: Feb. 15, 2017

(86) PCT No.: PCT/EP2017/000209
§ 371 (c)(1),
(2) Date: Oct. 10, 2019

(87) PCT Pub. No.: WO2017/140422
PCT Pub. Date: Aug. 24, 2017

(65) Prior Publication Data
US 2020/0369623 A1    Nov. 26, 2020

(30) Foreign Application Priority Data
Feb. 16, 2016 (EP) .................... 16000380

(51) Int. Cl.
C07D 237/32 (2006.01)
A61K 9/00 (2006.01)
A61K 9/12 (2006.01)
A61K 45/06 (2006.01)

(52) U.S. Cl.
CPC .......... *C07D 237/32* (2013.01); *A61K 9/0014* (2013.01); *A61K 9/0078* (2013.01); *A61K 9/12* (2013.01); *A61K 45/06* (2013.01); *C07B 2200/13* (2013.01)

(58) Field of Classification Search
CPC ........................... C07D 237/32; A61K 31/502
USPC ........................................ 514/248; 544/237
See application file for complete search history.

(56) References Cited

PUBLICATIONS

Henrich H. Paradies: "The crystal and molecular structure of 3-aminihydrazide (Luminol)", Berichie Der Bunsengesellschaft Fur Physikalische Chemie., vol. 96, No. 8, Jan. 1, 1992 (Jan. 1, 1992), pp. 1027-1031, XP055363618.
Helfried Neumann et al: "A New Efficient Synthesis of Substituted Luminols Using Multicomponent Reactions.", CHEMINFORM, vol. 59, No. 4, Aug. 31, 2004 (Aug. 31, 2004), pp. 431-438, XP055363616.
Thomas Martin et al: "Behind Crime Scenes: The Crystal Structure of Commercial Luminol", Crystal Growth & Design., vol. 16, No. 5, May 4, 2016 (May 4, 2016), pp. 3014-3018, XP055359896.
International Search Reportand Written Opinion dated Jul. 26, 2017 in corresponding International Application No. PCT/EP2017/000209.

*Primary Examiner* — Jeffrey H Murray
(74) *Attorney, Agent, or Firm* — Haug Partners LLP (57) ABSTRACT

A new method for producing a crystalline form of 5-amino-2,3-dihydro-1,4-phthalazinedione (luminol) is provided. Advantageous uses for this crystalline form as a detecting agent or as an agent for forensic purposes are disclosed, as well a pharmaceutical composition containing said crystalline form.

4 Claims, 5 Drawing Sheets

METHHOD FOR PRODUCING A CRYSTALLINE FORM OF 5-AMINO-2,3-DIHYDROPHTHALAZINE-1,4-DIONE

CROSS-REFERENCE TO RELATED APPLICATIONS

This application is the National Stage entry under 35 U.S.C. § 371 of International Application No. PCT/EP2017/000209 filed on Feb. 15, 2017, published on Aug. 24, 2017 under Publication Number WO 2017/140422, which claims the benefit of priority under 35 U.S.C. § 119 of European Patent Application Number 16000380.2 filed Feb. 16, 2016, the entireties of which are herein incorporated by reference.

Since decades, 5-Amino-2,3-dihydro-1,4-phthalazinedione (luminol) is used by crime scene investigators to detect traces of blood, even if someone has tried hard to clean or remove it (cf. Barni et al., Talanta 2007, 72, 896-913). The intense luminescence upon oxidation catalyzed by the iron in hemoglobin renders luminol a sensitive sensor. Beside its forensic use, numerous other applications ranging from environmental to medical have been established since the first report on the synthesis of luminol had appeared (A. J. Schmitz, Über das Hydrazid der Trimesinsäure and der Hemimellithsäure, Heidelberg, 1902). For instance, luminol is used for heavy metal detection or biosensing in bioanalytical chemistry (cf. Klopf and Nieman, Anal. Chem. 1983, 55, 1080-1083).

Alkaline salts of luminol have been structurally characterized only recently (Guzei et al., J. Coord. Chem. 2013, 66, 3722-3739), as the sodium salt of luminol has regained interest for its pharmaceutical activity. Na-luminolate shows great potential in immunomodulatory treatment of inflammatory and autoimmune diseases. Moreover, Na-luminolate shows a rich polymorphism with three crystal structures characterized so far (cf. WO 2011/107295 A1; PCT/EP2015/002555).

Figure 1:
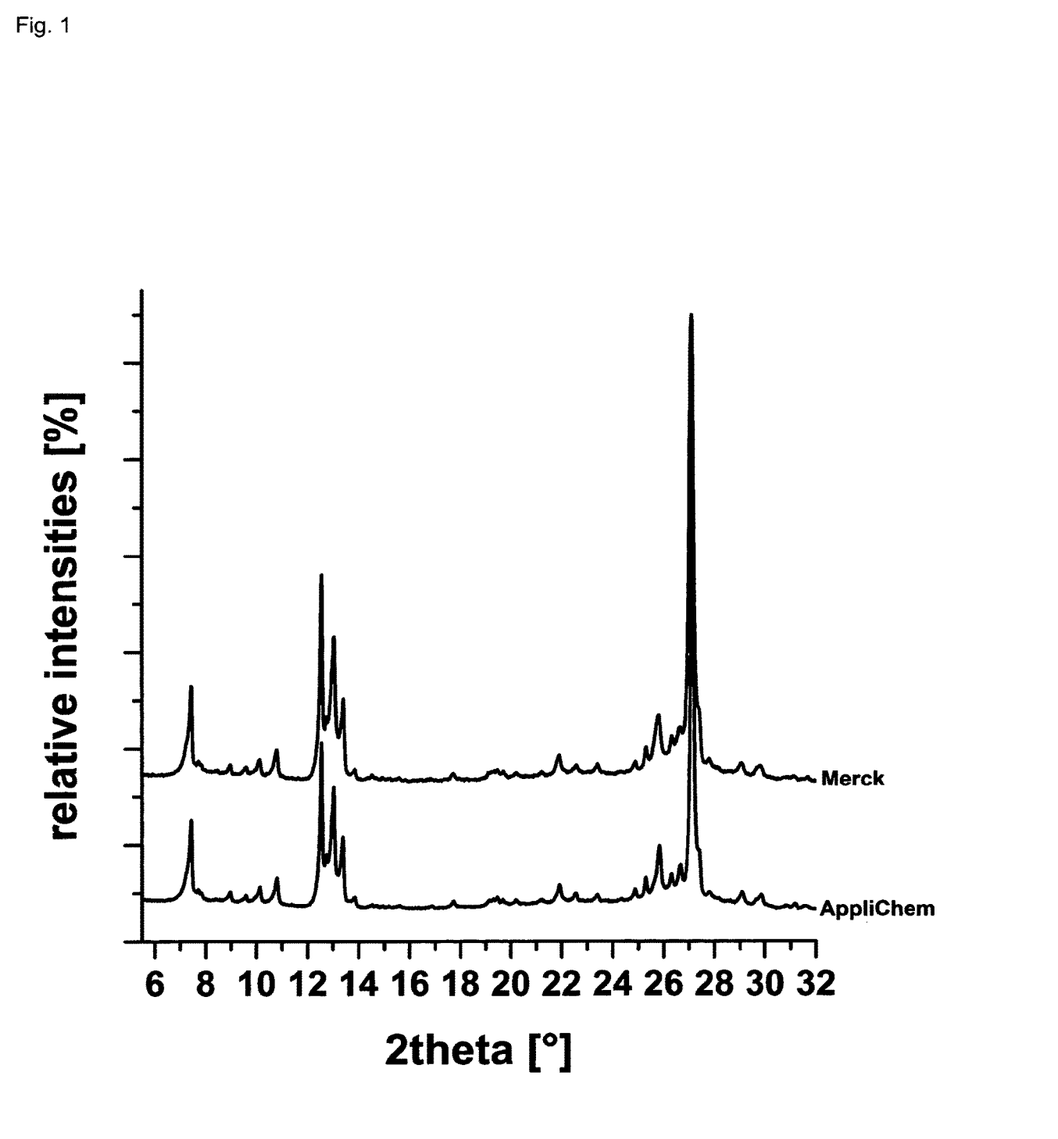
FIG. 1: XRPD diagrams of commercially available 5-amino-2,3-dihydro-1,4-phthalazinedione. Upper trace: 5-amino-2,3-dihydro-1,4-phthalazinedione purchased from Merck. Lower trace: 5-amino-2,3-dihydro-1,4-phthalazinedione purchased from AppliChem.

Commercially available luminol powders, however, suffer from mediocre crystallinity as indicated by ranges with rather broad and heavily overlapping reflections in PXRD (powder X-ray diffraction) patterns (cf. Ex. 1 and FIG. 1). This may not be a problem for some standard uses of luminol, as in forensic applications and/or aqueous luminol solutions, but there are a number of applications where it is highly desirable to use a pure crystalline form of luminol. In many pharmaceutical applications it is preferable to use the sodium salt of luminol, as neutral luminol is only poorly soluble in aqueous solutions at physiological pH (better in a mildly alkaline ambience, pH 8-11) and displays severe long-term stability problems therein. There are, however, some pharmaceutical applications and dosage forms for which a lipophilic molecule is preferable. Examples therefore are topical dosage forms, aerosols for an inhalative administration and retard dosage forms for a long-term release. For these purposes, it is highly preferable and even required by GMP standards and medical regulatory authorities to prove the purity, the reproducibility of the production method and the long-term stability of the active agent. Also in a variety of non-aqueous bioanalytical methods neutral luminol can be used. Their reliability and reproducibility depend also on a clearly defined and stable luminol molecule. This is achieved with a pure crystalline form of luminol.

A crystalline form of luminol was described by Paradies (Ber. Bunsen-Ges. Phys. Chem 1992, 96, 1027-1031). The use of this crystalline form of luminol, however, has been severely hampered by the cumbersome, tedious and thus costly production method of the crystalline form described by Paradies. He obtained this crystalline form only by controlled sublimation. Crystals were grown at 180° C. and at 5 Torr vacuum pressure in a closed environment on a cooling finger kept at 20° C. From the art it is known that crystals of organic molecular compounds grown by this method need several weeks (cf. J. Bernstein, Polymorphism in Molecular Crystals, Oxford, 2002, Chapter 3.5.1., p. 78). According to Paradies (1992) and Pawelski (Master thesis, Märkische Fachhochschule, Germany, 1989), other crystallization methods known in the art have apparently failed to grow phase pure luminol crystals.

Thus there is a need to provide a method for producing this crystalline form of luminol with less extensive technical equipment and preferably in a significantly shorter time.

Surprisingly, it was found that this task could be solved by the method for producing a crystalline form of 5-amino-2,3-dihydrophthalazine-1,4-dione according to the invention (Ex. 2). This method comprises the following steps:
 a) Dissolving 5-amino-2,3-dihydrophthalazine-1,4-dione in a refluxing ethanol-water solution having a range from 5:1 to 1:1 (v/v) at 50 to 100° C.,
 b) cooling the solution to room temperature over a period of 60 to 240 min,
 c) separating the precipitated crystalline product, and
 d) drying the crystalline product at room temperature over a period of 6 to 48 hours.

In an ensuing optional step e), the yielded crystalline form is resuspended one to three times in ethanol, is each time stirred, rewashed with ethanol and dried again.

Room temperature refers to a temperature range of 20±5° C.

This method yields phase-pure luminol crystals, i.e. with a high degree of crystallinity.

The standard analytical method for the characterization of crystals is a PXRD (powder X-ray diffraction) pattern. Characteristic D or 2-theta values can be derived from this pattern. "D" indicates the interplanar distances and "2-theta" indicates the 2-theta angle in degrees. The interplanar distance D (also: d) describes the perpendicular distance between two consecutive parallel lattice planes in a crystal. The Bragg angle theta ($\theta$) indicates the characteristic angle under which an incident X-ray (wave length: $\lambda$) is reflected at a lattice plane of a crystal and thus generates an X-ray diffraction pattern. Both parameters are linked via Bragg's law:

$$n\lambda = 2d\, \sin(\theta)$$

With the distinctive values for D and $\theta$ a crystal is necessarily and sufficiently characterized. The PXRD pattern of the crystals produced by the inventive method renders D and 2-theta values that substantially correspond to the values indicated by Paradies (given in Table 1).

TABLE 1

D values, 2-theta values and relative intensities I/Io

| D | 2-theta | I/Io (%) | I/Io (rel) |
|---|---|---|---|
| 11.3 | 7.8 | 10.77 | w |
| 11.1 | 7.9 | 13.39 | w |
| 6.9 | 12.8 | 34.35 | m |
| 6.8 | 13.0 | 32.69 | m |
| 6.3 | 14.0 | 17.54 | m |
| 5.6 | 15.8 | 6.81 | w |
| 3.5 | 25.2 | 23.28 | m |
| 3.4 | 25.9 | 13.42 | w |
| 3.4 | 26.3 | 5.22 | w |
| 3.2 | 27.6 | 7.95 | w |
| 3.2 | 27.8 | 100 | vst | vw = very weak ($0\% < I/I_0 \leq 5\%$)
w = weak ($5\% < I/I_0 \leq 15\%$)
m = medium ($15\% < I/I_0 \leq 35\%$)
st = strong ($35\% < I/I_0 \leq 75\%$)
vst = very strong ($75\% < I/I_0 \leq 100\%$)

Table 2 indicates the PXRD values found for the crystalline luminol form produced to the method according to the invention.

TABLE 2

D values, 2-theta values and relative intensities I/Io

| D | 2-theta | I/Io (%) | I/Io (rel) |
|---|---|---|---|
| 11.4 | 7.8 | 9.40 | w |
| 11.2 | 7.9 | 11.04 | w |
| 6.9 | 12.8 | 31.72 | m |
| 6.8 | 13.0 | 29.65 | m |
| 6.4 | 13.9 | 15.85 | m |
| 5.6 | 15.7 | 6.52 | w |
| 3.6 | 24.9 | 22.46 | m |
| 3.5 | 25.7 | 12.98 | w |
| 3.5 | 25.7 | 5.06 | w |
| 3.3 | 27.2 | 8.03 | w |
| 3.2 | 27.5 | 100 | vst | vw = very weak ($0\% < I/I_0 \leq 5\%$)
w = weak ($5\% < I/I_0 \leq 15\%$)
m = medium ($15\% < I/I_0 \leq 35\%$)
st = strong ($35\% < I/I_0 \leq 75\%$)
vst = very strong ($75\% < I/I_0 \leq 100\%$)

A comparison of these PXRD values shows that the crystalline luminol form produced by the method according to the invention is identical to the crystalline form described by Paradies. The deviations of the indicated values are in the usual range and may result from different diffractometers used herein.

Figure 2:
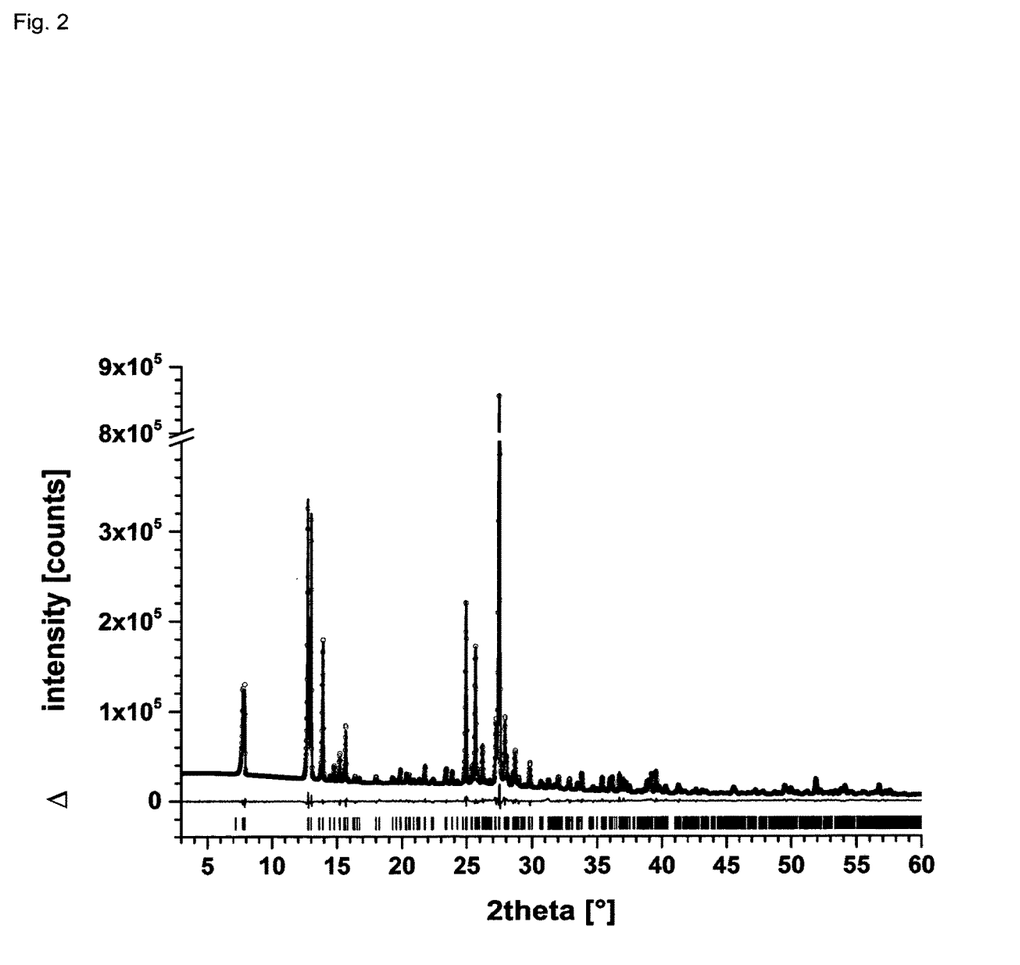
FIG. 2: Upper trace: XRPD diagram of the crystalline form of 5-amino-2,3-dihydro-1,4-phthalazinedione produced by the method according to the invention. Lower trace: The difference (A) to the XRPD diagrams from Exp. 1. Indicated are also the 2-theta reflections from the crystalline form of 5-amino-2,3-dihydro-1,4-phthalazinedione produced by the method according to the invention.

The PXRD pattern after Rietveld refinement of the crystalline luminol form produced by the method according to the invention is shown in FIG. 2. The significantly improved resolution of the structure and phase purity in comparison to commercially available luminol can be seen in the sharp and clearly resolved reflection peaks.

Figure 3:
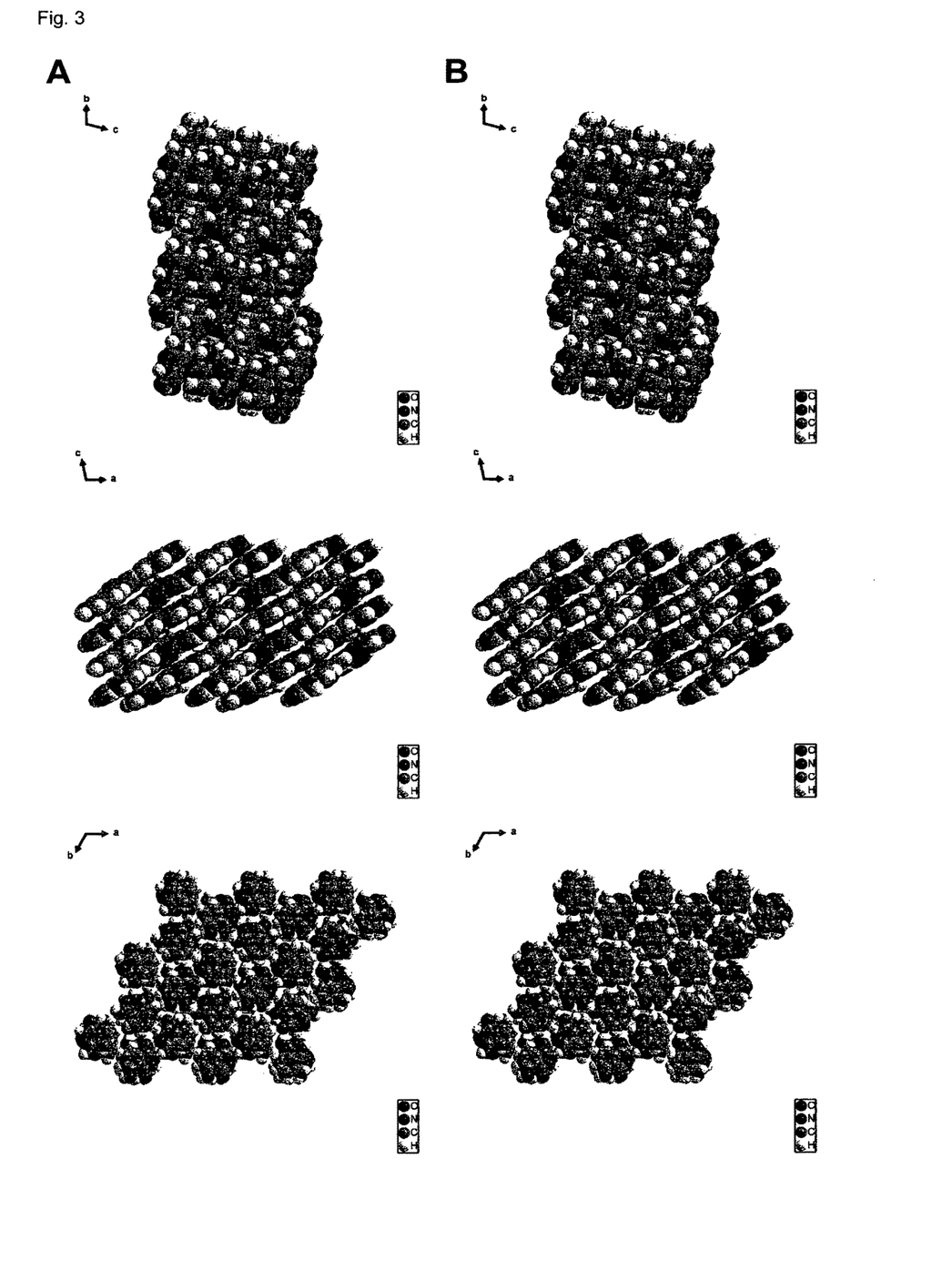
FIG. 3: A: Space-filling model of the molecular packing of the crystalline form of 5-amino-2,3-dihydro-1,4-phthalazinedione, calculated according to the values published by Paradies B: Space-filling model of the molecular packing of the crystalline form of 5-amino-2,3-dihydro-1,4-phthalazinedione produced by the method according to the invention Upper traces: along a axis; medium traces: along b axis; lower traces: along c axis, respectively.
Figure 4:
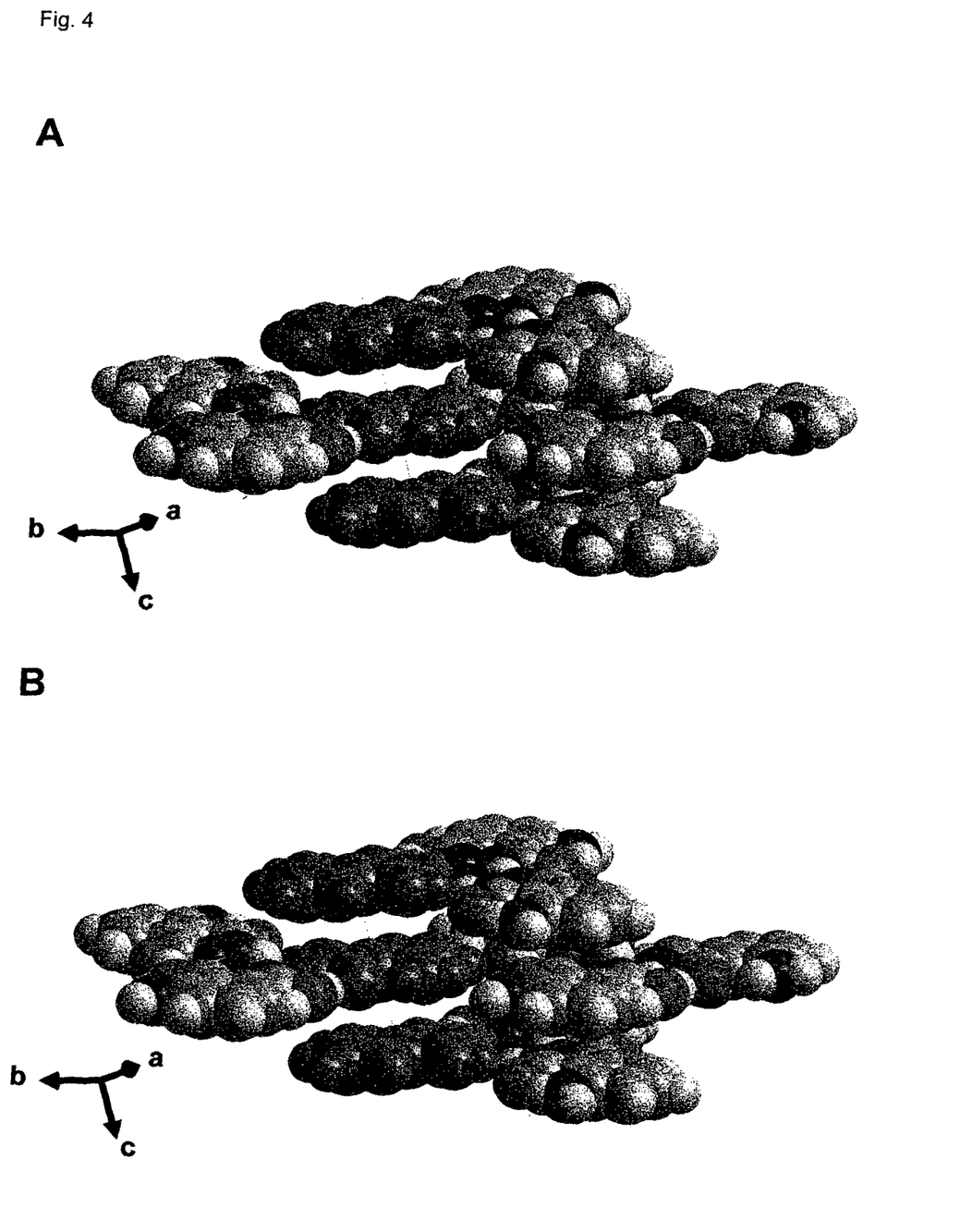
FIG. 4: A: Trimer stacking model of the molecular packing of the crystalline form of 5-amino-2,3-dihydro-1,4-phthalazinedione, calculated according to the values published by Paradies B: Trimer stacking model of the molecular packing of the crystalline form of 5-Amino-2,3-dihydro-1,4-phthalazinedione produced by the method according to the invention

FIG. 3 A+B show a comparison of the molecular packing calculated for the respective PXRD values for the crystalline form published by Paradies (A) and for the crystalline form produced by the method according to the invention (B). In FIG. 4 shifted stacking of trimers in adjacent layers is depicted, respectively. As can be seen therein, an identical layer stacking was found. Also these models corroborate the identity of both crystalline forms.

The ethanol-water ratio of step a) of the inventive method may range from 5:1 to 1:1, preferred 4:1 to 2:1 and most preferred 3:1 (v/v, respectively).

The temperature range for the dissolution step a) of the inventive method is from 50 to 100° C., preferred from 70 to 90° C., and most preferred the temperature is 80° C.

The time range for the cooling down step b) of the inventive method is from 60 to 240 min, preferred from 90 to 180 min, and most preferred the period is 120 min.

The time range for the drying step d) of the inventive method is from 6 to 48 hours, preferred from 10 to 24 hours, and most preferred is a period of 12 hours.

In a preferred embodiment, the crystalline luminol form produced by the method according to the invention has a crystal water content ≤0.4%. Such a low crystal water content corresponds to phase purity of the crystalline form.

In a preferred embodiment, the ethanol used in the method according to the invention has a degree of purity ≥98%.

In a preferred embodiment, the method according to the invention comprises the following steps:
  a) Dissolving 5-amino-2,3-dihydrophthalazine-1,4-dione in a refluxing ethanol-water solution (3:1, v/v) at 80° C.,
  b) cooling the solution to room temperature over a period of 120 min,
  c) separating the precipitated crystalline product, and
  d) drying the crystalline product at room temperature for 12 hours.

In alternative embodiments the drying step e) is varied by drying the washed precipitate from step d) in a vacuum dryer at 25-200° C./1100 to 5 mbar, in a freeze dryer, wherein the residual solvent content in the previously frozen crystallization product is removed by sublimation at 0.1 mbar, or in a rotary evaporator at 25-180° C./1050-1 mbar, until constant masses are obtained.

Thus the inventive method for producing a crystalline form of 5-amino-2,3-dihydrophthalazine-1,4-dione provides a number of advantages in respect to the state of the art:
  much less complex technical equipment is needed
  therefore the production costs with the inventive method are significantly less
  higher reproducibility by a simpler method (less potential failures)
  significantly less time is needed for obtaining the crystalline form The present invention relates also to the product of the inventive method. Thus a crystalline form of 5-amino-2,3-dihydrophthalazine-1,4-dione is disclosed that is characterized by the following crystallography values determined by means of powder X-ray diffraction:
  d values: 11.4; 11.2; 6.9; 6.8; 6.4; 5.6; 3.6; 3.5; 3.5; 3.3; 3.2 and
  2-theta values: 7.8; 7.9; 12.8; 13.0; 13.9; 15.7; 24.9; 25.7; 25.7; 27.2; 27.5,
wherein this crystalline form has been produced by the method according to the invention.

There is a broad range of analytical applications of luminol, either in biosciences or in material sciences. In most cases, the chemiluminescence of luminol upon oxidation is used as a detective tool, in a few cases also its fluorescence. In particular, if small amounts of a substance shall be detected an ultrasensitive detecting method is needed. Such ultrasensitive methods require a strictly defined amount and structure of the detecting agent and a reliable and reproducible manufacturing method. Therefore, especially for these methods it is preferable to use a phase pure crystalline form of luminol instead of the commercially available form. In Khan et al. (2015, Appl Biochem Biotechnol 173, pp. 333-355) a comprehensive overview of the current analytical methods using luminol as a detective agent is given. It covers such fields as the use in clinical laboratories, clinical research, immunoassays, as biosensors, in oncology, nucleic acid assays, reporter gene-based assays, cellular chemiluminescence for the localization of certain cells or molecules, protein quantification, environmental monitoring, $Hg^{2+}$ and $Cu^{2+}$ detection and quantification, forensic science, DNA detection, blood detection in a hospital ambience and pharmaceutical analysis, e.g. flow injection, drug tracing and the pharmacokinetics of an active agent.

In all these fields a crystalline form of luminol produced by the method according to the invention can be used.

Therefore, the present invention relates also to the use of said crystalline luminol form produced by the method according to the invention for use as a detecting agent.

In particularly preferred embodiments crystalline luminol form produced by the method according to the invention is used in detection methods used in non-aqueous environments Therein, luminol can be used directly in its crystalline form.

Examples are sodium dodecyl sulfate polyacrylamide gel electrophoresis (SDS-PAGE), capillary electrophoresis, test systems with molecules fixated on polymeric membranes, microarray based systems, mass spectrometry, electron microscopy, or cathodic electrogenerated chemiluminescence of luminol (ECL) on a glassy carbon electrode (cf. Haghighi et al. 2015, Electrochimica Acta 154, 259-265).

Further particularly preferred analytical methods include the use in detection assays using DMSO in moderately strong alkaline protic solvents (pH 8-11) in water or lower alcohols, as neutral luminol can be easily solved therein.

Moreover, in particularly preferred embodiments the present invention relates also to the use of said crystalline luminol form produced by the method according to the invention for use for forensic purposes, as reviewed in Pax, International Association, Bloodstain Pattern Analysis. Newsletter 2205, pp. 11-15.

One of the most important application areas for phase pure luminol crystals is a pharmaceutical use. In general, a pharmaceutically active agent is administered to a patient in form of a pharmaceutically acceptable dosage form. Therefore the present application refers also to a pharmaceutical composition comprising a crystalline form of 5-amino-2,3-dihydrophthalazine-1,4-dione produced by the method according to the invention, being characterized by the following crystallography values determined by means of powder X-ray diffraction:
d values: 11.4; 11.2; 6.9; 6.8; 6.4; 5.6; 3.6; 3.5; 3.5; 3.3; 3.2 and
2-theta values: 7.8; 7.9; 12.8; 13.0; 13.9; 15.7; 24.9; 25.7; 25.7; 27.2; 27.5
and at least one pharmaceutically acceptable excipient.

The term "pharmaceutical composition" means according to the invention at least one active agent according to the invention in a pharmacologically suitable dose and dosage form together with at least one suitable pharmaceutically acceptable excipient or carrier substance as well as optionally at least one further pharmaceutical agent known in the state of the art.

The term "excipient" is used in this application to describe each component of a pharmaceutical composition in addition to the crystalline form of luminol according to the invention. The selection of a suitable excipient depends on various factors, such as dosage form and dose as well as the influence on the solubility and stability of the composition by the excipient itself.

The term "action" describes the inherent specific mode of action of the respective agent.

The terms "effect" and "therapeutic effect", regarding at least one active agent according to the invention refer to causally occurring beneficial consequences for the organism, to which the at least one active agent has been administered.

In terms of the application, "therapeutically effective dose" means that a sufficient dose of the at least one active agent according to the invention is administered to a living being or to a patient in need of such a treatment.

The terms "joint administration", "combined administration" or "simultaneous administration" of the at least one pharmaceutical agent according to the invention and of at least one pharmaceutical agent from the state of the art comprise the administration of the mentioned agents at the same time or at points in time close to each other, as well as administrations of said agents at different times within a coherent experiment. The chronological order of the administration of said agents is not limited by these terms. Those skilled in the art will have no difficulties to deduce the described administrations in respect to their chronological or local order from his knowledge and experience.

The term "living being" refers to every animal, especially vertebrate, in particular primate, and most preferred human. A "patient" in terms of the application is a living being who suffers from a definable and diagnosable disease, or has a predisposition therefor, and to whom a suitable active agent is administered for the purpose of prophylaxis or therapy.

In the sense of this application the terms "medicine" or "medical" shall refer to human medicine as to veterinary medicine as well.

The terms "prophylaxis", "treatment" and "therapy" comprise the administration of at least one suitable active agent according to the invention, alone or in combination with at least one further pharmaceutical agent known in the art, to a living being, in order to prevent the development of a certain disease, to inhibit, and to alleviate the symptoms, or to initiate a healing process of the respective disease.

Pharmaceutical formulations of the compounds for use according to the invention can be administered by any suitable way, e.g. orally (incl. buccally and sublingually), rectally, vaginally, nasally, inhalatory, respiratory, alveolary, topically (incl. buccally, sublingually, conjunctivally or transdermally), or parenterally (incl. intraperitoneally, subcutaneously, intramuscularly, intravenously, intraarterially or intradermally).

Formulations can be produced by any method known in the pharmaceutical field by combining the active agent with at least one carrier or excipient.

Thus the present application refers also to a pharmaceutical composition containing a crystalline form of luminol produced by the method according to the invention and at least one pharmaceutically acceptable excipient, wherein said at least one pharmaceutically acceptable excipient is selected from a group comprising carriers, binding agents, lubricants, glidants, disintegrants, colorants, buffers, preservatives, solubilizing agents, emulsifiers, permeation enhancers, antioxidants, diluents, pH-regulators, fatiquors, solvents, consistency enhancers, hydrotopes, sweeteners, acidifiers, thickening agents, flavoring substances, and aromatic substances.

Eligible carriers are all carriers known in the art and combinations thereof. In solid dosage forms they can be for example plant and animal fats, waxes, paraffins, starch, tragacanth, cellulose derivatives, polyethylene glycols, silicones, bentonites, silica, talcum, zinc oxide or mixtures of the aforementioned substances. For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethyl glycols, fatty acid esters of sorbitan, or mixtures of the aforementioned substances. Suspensions according to the invention may use carriers known in the art such as diluents (e.g. water, ethanol or propylene glycol), ethoxylized isostearyl alcohols, polyoxyethylene and polyoxyethylene sorbitan esters, microcrystalline cellulose, bentonites, agar agar, tragacanth.

Pharmaceutical formulations suitable for oral dosage forms may be administered as separate units such as capsules, tablets, sugar-coated tablets or pills; powders or granulates; juices, syrups, drops, teas, solutions or suspensions in aqueous or non-aqueous liquids; edible foams or mousses; or in oil-in-water or water-in-oil in lotions.

For example, in an oral dosage form such as a tablet or capsule the active agent can thus be combined with an oral, non-toxic and pharmaceutically acceptable inert carrier such as ethanol, glycerin or water. Powders are produced by grinding the compound to a suitably tiny particle size and mixing them with a pharmaceutical carrier ground in a similar manner, e.g. an edible carbohydrate such as starch or mannitol. A flavor, preservative, dispersant or colorant can also be present.

Capsules can be produced by producing a powder mixture as described before and filling it into shaped gelatine covers. Glidants and lubricants such as highly dispersed silica, talcum, magnesium stearate, calcium stearate or polyethylene glycol can be added to the powder mixture as solids. A disintegrants or solubilizer such as agar agar, calcium carbonate or sodium carbonate can be added likewise in order to improve the availability of the medication after intake of the capsule. Additionally, suitable binding agents and/or colorants can be added to the mixture, if desirable or necessary.

The term binding agents refers to substances that bind powders or glue them together, rendering them cohesive through granule formation. They serve as a "glue" of the formulation. Binding agents increase the cohesive strength of the provided diluent or filler.

Suitable binding agents are starch from wheat, corn, rice or potato, gelatine, naturally occurring sugars such as glucose, sucrose or beta-lactose, sweeteners from corn, natural and synthetic gums such as acacia, tragacanth or ammonium calcium alginate, sodium alginate, carboxymethyl cellulose, sodium carboxymethyl cellulose, hydroxypropyl carboxymethyl cellulose, polyethylene glycol, polyvinyl pyrrolidone, magnesium aluminium silicate, waxes and others. The percentage of the binding agent in the composition can range from 1-30% by weight, preferred 2-20% by weight, more preferred 3-10% by weight and most preferred 3-6% by weight.

The term lubricants refers to substances that are added to the dosage form in order to facilitate tablets, granulates etc. to be released from the press mold or the outlet nozzle. They diminish friction or abrasion. Lubricants are usually added shortly before pressing, as they should be present on the surface of the granules and between them and the parts of the press mold. The amount of the lubricant in the composition may vary between 0.05 and 15% per weight, preferred between 0.2 and 5% per weight, more preferred between 0.3 and 3% per weight, most preferred between 0.3 and 1.5% per weight.

Suitable lubricants are a.o. sodium oleate, metal stearates such as sodium stearate, calcium stearate, potassium stearate and magnesium stearate, stearic acid, sodium benzoate, sodium acetate, sodium chloride, boric acid, waxes having a high melting point, polyethylene glycol.

Glidants are materials that prevent a baking of the respective agents and improve the flow characteristics of granulations so that the flow is smooth and constant.

Suitable glidants comprise silicon dioxide, magnesium stearate, sodium stearate, starch and talcum. The amount of the glidant in the composition may vary between 0.01 and 10% per weight, preferred between 0.1 and 7% per weight, more preferred between 0.2 and 5% per weight, most preferred between 0.5 and 2% per weight.

The term disintegrant refers to substances added to a composition in order to facilitate their breaking apart.

Suitable disintegrants can be selected from the group comprising starch, cold water-soluble starches such as carboxymethyl starch, cellulose derivatives such as methyl cellulose and sodium carboxymethyl cellulose, microcrystalline cellulose and cross-linked microcrystalline celluloses such as croscarmellose sodium, natural and synthetic gums such as guar, agar, karaya (Indian tragacanth), locust bean gum, tragacanth, clays such as bentonite, xanthan gum, alginates such as alginic acid and sodium alginate, foaming compositions a.o. Moisture expansion is supported by for example starch, cellulose derivatives, alginates, polysaccharides, dextrans, and cross-linked polyvinyl pyrrolidone. The amount of the disintegrant in the composition may vary between 1 and 40% per weight, preferred between 3 and 20% per weight, most preferred between 5 and 10% per weight.

Colorants are excipients that bestow a colorization to the composition or dosage form. These excipients can be food colorants. They can be adsorbed on a suitable adsorption means such as clay or aluminium oxide. The amount of the colorant may vary between 0.01 and 10% per weight of the composition, preferred between 0.05 and 6% per weight, more preferred between 0.1 and 4% per weight, most preferred between 0.1 and 1% per weight.

Suitable food colorants are curcumin, riboflavin, riboflavin-5'-phosphate, tartrazine, alkanin, quinolione yellow WS, Fast Yellow AB, riboflavin-5'-sodium phosphate, yellow 2G, Sunset yellow FCF, orange GGN, cochineal, carminic acid, citrus red 2, carmoisine, amaranth, Ponceau 4R, Ponceau SX, Ponceau 6R, erythrosine, red 2G, Allura red AC, lndathrene blue RS, Patent blue V, indigo carmine, Brilliant blue FCF, chlorophylls and chlorophyllins, copper complexes of chlorophylls and chlorophyllins, Green S, Fast Green FCF, Plain caramel, Caustic sulphite caramel, ammonia caramel, sulphite ammonia caramel, Black PN, Carbon black, vegetable carbon, Brown FK, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8'-carotenic acid, flavoxanthin, lutein, cryptoxanthin, rubixanthin, violaxanthin, rhodoxanthin, canthaxanthin, zeaxanthin, citranaxanthin, astaxanthin, betanin, anthocyanins, saffron, calcium carbonate, titanium dioxide, iron oxides, iron hydroxides, aluminium, silver, gold, pigment rubine, tannin, orcein, ferrous gluconate, and ferrous lactate.

Tablets are formulated by producing, granulating or dry-pressing a powder mixture, adding a lubricant and a disintegrants and pressing the mixture to a tablet. A powder mixture is produced by mixing a suitably ground compound with a diluent or a base as described before, and if applicable, with a binding agent such as carboxymethyl cellulose, an alginate, gelatine or polyvinyl pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acacia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps.

Liquid dosage forms comprise solutions, suspensions and emulsions. Examples are water and water/propylene glycol solutions for parenteral injections, or the addition of a sweetener or opacifier for oral solutions, suspensions and emulsions. Liquid dosage forms may also comprise solutions for intranasal administration.

Moreover, buffers or buffer solutions are preferred for liquid formulations, in particular for pharmaceutical liquid formulations. The terms buffer, buffer system and buffer solution, in particular of an aqueous solution, refer to the capacity of the system to resist a pH change by the addition of an acid or a base, or by dilution with a solvent. Preferred buffer systems may be selected from the group comprising formate, lactate, benzoic acid, oxalate, fumarate, aniline, acetate buffer, citrate buffer, glutamate buffer, phosphate buffer, succinate, pyridine, phthalate, histidine, MES (2-(N-morpholino)ethanesulfonic acid, maleic acid, cacodylate (dimethyl arsenate), carbonic acid, ADA (N-(2-acetamido) imino diacetic acid, PIPES (4-piperazine-bis-ethanesulfonic acid), BIS-TRIS propane (1,3-bis[tris(hydroxymethyl)methylaminol] propane), ethylene diamine, ACES (2-[(amino-2-oxoethyl)amino]ethanesulfonic acid), imidazol, MOPS (3-(N-morphino)-propanesulfonic acid, diethyl malonic acid, TES (2-[tris(hydroxymethyl)methyl]aminoethanesulfonic acid, HEPES (N-2-hydroxyethylpiperazine-N'-2-ethanesulfonic acid), as well as other buffers with a $pK_a$ between 3.8 and 7.7.

Preferred are carbonic acid buffers such as acetate buffer and dicarboxylic acid buffers such as fumarate, tartrate and phthalate as well as tricarboxylic acid buffers such as citrate.

A further group of preferred buffers are inorganic buffers such as sulfate hydroxide, borate hydroxide, carbonate hydroxide, oxalate hydroxide, calcium hydroxide and phosphate buffers. Another group of preferred buffers are nitrogen-containing puffers such as imidazol, diethylene diamine and piperazine. Furthermore preferred are sulfonic acid buffers such as TES, HEPES, ACES, PIPES, [(2-hydroxy-1,1-bis-(hydroxymethyl)ethyl)amino]-1-propanesulfonic acid (TAPS), 4-(2-hydroxyethyl)piperazine-1-propanesulfonic acid (EEPS), 4-morpholino-propanesulfonic acid (MOPS) and N,N-bis-(2-hydroxyethyl)-2-aminoethanesulfonic acid (BES). Another group of preferred buffers are glycine, glycyl-glycine, glycyl-glycyl-glycine, N,N-bis-(2-hydroxyethyl)glycine and N-[2-hydroxy-1,1-bis(hydroxymethyl)ethyl]glycine (tricine). Preferred are also amino acid buffers such as glycine, alanine, valine, leucine, isoleucine, serine, threonine, phenylalanine, tyrosine, tryptophan, lysine, arginine, histidine, aspartate, glutamate, asparagine, glutamine, cysteine, methionine, proline, 4-hydroxy proline, N,N,N-trimethyllysine, 3-methyl histidine, 5-hydroxy-lysine, o-phosphoserine, gamma-carboxyglutamate, [epsilon]-N-acetyl lysine, [omega]-N-methyl arginine, citrulline, ornithine and their derivatives.

Preservatives for liquid dosage forms or supplements can be used on demand. They may be selected from the group comprising sorbic acid, potassium sorbate, sodium sorbate, calcium sorbate, methyl paraben, ethyl paraben, methyl ethyl paraben, propyl paraben, benzoic acid, sodium benzoate, potassium benzoate, calcium benzoate, heptyl p-hydroxybenzoate, sodium methyl para-hydroxybenzoate, sodium ethyl para-hydroxybenzoate, sodium propyl para-hydroxybenzoate, benzyl alcohol, benzalkonium chloride, phenylethyl alcohols, cresols, cetylpyridinium chloride, chlorobutanol, thiomersal (sodium 2-(ethylmercurithio) benzoic acid), sulfur dioxide, sodium sulphite, sodium bisulphite, sodium metabisulphite, potassium metabisulphite, potassium sulphite, calcium sulphite, calcium hydrogen sulphite, potassium hydrogen sulphite, biphenyl, orthophenyl phenol, sodium orthophenyl phenol, thiabendazole, nisin, natamycin, formic acid, sodium formate, calcium formate, hexamine, formaldehyde, dimethyl dicarbonate, potassium nitrite, sodium nitrite, sodium nitrate, potassium nitrate, acetic acid, potassium acetate, sodium acetate, sodium diacetate, calcium acetate, ammonium acetate, dehydroacetic acid, sodium dehydroacetate, lactic acid, propionic acid, sodium propionate, calcium propionate, potassium propionate, boric acid, sodium tetraborate, carbon dioxide, malic acid, fumaric acid, lysozyme, copper-(II)-sulfate, chlorine, chlorine dioxide and other suitable substances or compositions known to the person skilled in the art.

A particularly preferred pharmaceutical composition is a lyophilisate (a dry-freezed formulation) suitable for administration via inhalation or intravenous injection. For its production, a compound for use according to the invention is solubilized in a 4-5% mannitol solution, whereupon this solution is lyophilized. The mannitol solution can be prepared in a suitable buffer solution, as described before. Further examples of suitable cryo/lyoprotectants (also fillers or stabilizers) are thiol-free albuminin, immunoglobulin, polyalkylene oxide (i.e. PEG, polypropylene glycol), Trehalose, glucose, sucrose, sorbitol, dextran, maltose, raffinose, stachyose and other saccharides. Mannitol is preferred. They can be used in the lyophilization process in usual amounts known to a person skilled in the art.

For the production of a dosage form of a suppository containing a compound for use according to the invention waxes with a low melting point as well as a mixture of fatty acid glycerides such as cocoa butter are first melted, then 5-amino-2,3-dihydro-1,4-phthalazinedione is homogenously dispersed under stirring or other mixing methods. The molten homogeneous mixture is transferred to suitable moulds and then cooled down until solidification.

For topical applications containing a compound for use according to the invention creams, emulsions, lotions, gels, hydrogels, pastes, powders, ointments, liniment, films, liposomes, dermal patches, transdermal patches, transdermal sprays or suspensions are suitable.

Suitable as surface-active solubilizing agents (solubilizers) are for example diethylene glycol monoethyl ester, polyethyl propylene glycol co-polymers, cyclodextrins such as α- and β-cyclodextrin, glyceryl monostearates such as Solutol HS 15 (Macrogol-15-hydroxystearate from BASF, PEG 660-15 hydroxystearates), sorbitan esters, polyoxyethylene glycol, polyoxyethylene sorbitanic acid esters, polyoxyethylene sorbitan monoleate, polyoxyethylene oxystearic acid triglyceride, polyvinyl alcohol, sodium dodecyl sulfate, (anionic) glyceryl monooleates etc.

Emulsifiers can be selected for example from the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters, polyoxyethene sorbitan monolaurate, polyoxyethene sorbitan monooleate, polyoxyethene sorbitan monopalmitate, polyoxyethene sorbitan monostearate, polyoxyethene sorbitan tristearate, polyoxyethene stearate, polyvinyl alcohol, metatartaric acid, calcium tartrate, alginic acid, sodium alginate, potassium alginate, ammonium alginate, calcium alginate, propane-1,2-diol alginate, carrageenan, processed eucheuma seaweed, locust bean gum, tragacanth, acacia gum, karaya gum, gellan gum, gum ghatti, glucomannane, pectin, amidated pectin, ammonium phosphatides, brominated vegetable oil, sucrose acetate isobutyrate, glycerol esters of wood rosins, disodium phosphate, trisodium diphosphate, tetrasodium diphosphate, dicalcium diphosphate, calcium dihydrogen diphosphate, sodium triphosphate, pentapotassium triphosphate, sodium polyphosphates, sodium calcium polyphosphate, calcium polyphosphates, ammonium polyphosphate, beta-cyclodextrin, powdered cellulose, methyl cellulose, ethyl cellulose, hydroxypropyl cellulose, hydroxypropyl methylcellulose, ethyl methyl cellulose, carboxymethyl cellulose, sodium carboxymethyl cellulose, ethyl hydroxyethyl cellulose, croscarmellose, enzymically hydrolyzed carboxymethyl cellulose, mono- and diglycerides of fatty acids, glyceryl monostearate, glyceryl distearate, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, mono- and diacetyl tartaric acid esters of mono- and diglycerides of fatty acids, mixed acetic and tartaric acid esters of mono- and diglycerides of fatty acids, succinylated monoglycerides, sucrose esters of fatty acids, sucroglycerides, polyglycerol esters of fatty acids, polyglycerol polyricinoleate, propane-1,2-diol esters of fatty acids, propylene glycol esters of fatty acids, lactylated fatty acid esters of glycerol and propane-1, thermally oxidized soy bean oil interacted with mono- and diglycerides of fatty acids, dioctyl sodium sulphosuccinate, sodium stearoyl-2-lactylate, calcium stearoyl-2-lactylate, stearyl tartrate, stearyl citrate, sodium stearoyl fumarate, calcium stearoyl fumarate, stearyl tartrate, stearyl citrate, sodium stearoyl fumarate, calcium stearoyl fumarate, sodium laurylsulfate, ethoxylated mono- and diglycerides, methyl glucoside-coconut oil ester, sorbitan monostearate, sorbitan tristrearate, sorbitan monolaurate, sorbitan monooleate, sorbitan monopalmitate, sorbitan trioleate, calcium sodium polyphosphate, calcium polyphosphate, ammonium polyphosphate, cholic acid, choline salts, distarch glycerol, starch sodium octenyl succinate, acetylated oxidized starch.

Preferred are glycerin monooleate, stearic acid, phospholipids such as lecithin.

Suitable triglycerides are medium-chain and high molecular triglycerides. Medium-chain triglycerides are glycerin esters of fatty acids with only 6-12 carbon atoms, such as caprylic/capric acid triglyceride. High molecular triglycerides are glycerin fatty acid esters with long-chained fatty acids, e.g. triglyceride mixtures extracted from several naturally occurring fats. Preferred are medium-chain triglycerides, in particular caprylic/capric acid triglyceride.

Permeation enhancers are often used in topical dosage forms. Suitable permeation enhancers comprise all pharmaceutically acceptable permeation enhancers known in the art, such as, without being limiting, azones such as laurocapran, 1-dodecylazacycloheptan-2-one; sulphoxides such as dimethylsulphoxide, DMAC, DMF; pyrrolidones such as 2-pyrrolidone, N-methyl-2-pyrrolidone; alcohols such as ethanol, 1,2-propandiol or decanol; glycols such as propylene glycol, diethylene glycol, tetraethylene glycol; fatty acids such as oleic acid, lauric acid, sodium lauryl sulfate, myristic acid, isopropyl myristic acid, capric acid; nonic surfactants such as polyoxyethylene-2-oleyl ether, polyoxyethylene-2-stearyl ether; terpenes; terpenoids; oxazolidinones; urea; ceramide analogs, azone analogs, menthol derivatives, etherified derivatives, esterified derivatives, transkarbams, carbamate salts, TXA derivatives, DDAIP (dodecyl 2-(dimethylamino) propanoate), DDAK, natural essential oils (all of them listed in Chen et al. (2014) Asian J. Pharm. Sc. 9, 51-64); citric acid esters such as triethyl citrate; hydrophobin polypeptides; alpha-bisabolol; dimethyl isosorbide (Arlasolve® DMI); ethoxydiglycol. Preferred is 1,2-propandiol.

Typical examples for preservatives suitable for topical applications are e.g. benzyl benzoate, benzoic acid, benzyl alcohol, benzalkonium chloride, N-cetyl-N—N-trimethyl-ammonium bromide (Cetrimid, Merck), chlorhexidine, chlorbutanol, chlorcresol, imiudurea, parabens such as methyl, ethyl, propyl or butyl paraben, sodium methylparaben, sodium propylparaben, potassium sorbate, sodium benzoate, sodium propionate, phenol, phenoxyethanol, phenylethyl alcohol, phenylmercuriacetate, phenylmercuriborate, phenylmercurinitrate, sorbic acid or Thiomersal (sodium methylmercurithiosalicylate). Preferred are methylparaben, propylparaben as well as sodium methylparaben and sodium propylparaben.

The addition of antioxidants is particularly preferable in topical dosage forms. Suitable examples for antioxidants include sodium metabisulfite, alpha-tocopherol, ascorbic acid, maleic acid, sodium ascorbate, ascorbyl palmitate, butylated hydroxyanisol, butylated hydroxytoluol, fumaric acid or propyl gallate. Preferred is the use of sodium metabisulfite.

Suitable pH-regulators for topical dosage forms are e.g. sodium hydroxide, hydrochloric acid, buffer substances such as sodium dihydrogen phosphate or disodium hydrogenphosphate.

Cream preparations may also contain other excipients and additives, such as fatiquors, solvents, consistency enhancers or hydrotopes for improving the flow characteristics. Herein single as well as several substances from the same group of additives or excipients may be present in the mixture.

Suitable fatiquors are e.g. oleic acid decylester, hydrated castor oil, light mineral oil, mineral oil, polyethylene glycol, sodium laurylsulfate.

Suitable solvents are corn oil, cottonseed oil, peanut oil, sesame oil, soybean oil, ethyl oleate, glycerin, isopropyl myristate, isopropyl palmitate, polyethylene glycol or polypropylene glycol.

Consistency enhancers are e.g. cetyl alcohol, cetyl ester wax, hydrated castor oil, microcrystalline waxes, non-ionic emulsifier waxes, beeswax, paraffin or stearylic alcohol.

Suitable hydrotopes are alcohols such as ethanol, isopropyl alcohol or polyols such as glycerin.

Preparations according to the invention may further contain additives. They are preferably selected from aromatic and flavoring substances, in particular essential oils, vitamins and galenics excipients selected from sugars, sugar substitutes, nutritional sweeteners, acidifiers, solubilizers such as water, glycol, glycerin, thickening agents, sweeteners, colorants or preservatives or combinations thereof, also depending from the galenical dosage form.

Suitable aromatic and flavoring substances comprise above all essential oil that can be used for this purpose. In general, this term refers to volatile extracts from plants or parts of plants with the respective characteristic smell. They can be extracted from plants or parts of plants by steam distillation.

Examples are: Essential oils, respectively aromatic substances from sage, cloves, chamomile, anise, star anise, thyme, tea tree, peppermint, mint oil, menthol, cineol, *eucalyptus* oil, mango, figs, lavender oil, chamomile blossoms, pine needles, cypress, oranges, rosewood, plum, currant, cherry, birch leaves, cinnamon, limes, grapefruit, tangerine, juniper, valerian, lemon balm, lemon grass, palmarosa, cranberry, pomegranate, rosemary, ginger, pineapple, guava, *echinacea*, ivy leave extract, blueberry, kaki, melons etc. or mixtures thereof, as well as mixtures of menthol, peppermint and star anise oil or menthol and cherry flavor.

These aromatic or flavoring substances can be included in the range of 0.0001 to 10% per weight (particularly in a composition), preferred 0.001 to 6% per weight, more preferred 0.001 to 4% per weight, most preferred 0.01 to 1% per weight, with regard to the total composition. Application- or single case-related it may be advantageous to use differing quantities.

Subject matter of the invention is also the crystalline form of luminol produced by the method according to the invention, optionally in the combinations of active agents, as described before, for use for the production of a formulation for oral administration, a formulation as lyophilisate, a liquid formulation or a topical formulation.

The previously described formulations and pharmaceutical compositions can contain in addition to the crystalline form of luminol produced by the method according to the invention at least one further active agent.

This at least one further active agent can be selected from the group comprising steroidal and non-steroidal anti-inflammatory agents, immunomodulators, immunosuppressive agents, antibiotics, anti-infective agents, antiviral agents, antimycotics, analgesics, local anesthetics, anticoagulants, thrombocyte aggregation inhibitors, muscle relaxants, tonic agents and anabolic agents. Such a combination of active agents can be used for prophylactic and/or therapeutic purposes in a person in need of such an administration.

Suitable examples for steroidal anti-inflammatory agents comprise corticosteroids, glucocorticoids, cortisone, cortisone acetate, hydrocortisone, hydrocortisone acetate, dexamethasone, betamethasone, prednisone, prednisolone, methylprednisolone, deltasone, triamcinolone, tixocortol pivalate, mometasone, amcinonide, budesonide, desonide, fluociconide, fluocinolone, halcinonide, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, flunisolide, fluticasone furoate, fluticasone propionate, triamcinolone acetonide, beclomethasone dipropionate.

Suitable examples for non-steroidal anti-inflammatory drugs (NSAIDs) comprise acetylsalicylic acid, salicylic acid and salicylates, paracetamol (acetaminophen), salsalate, diflunisal, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, celexoxib, rofecoxib, valdecoxib, parecoxib, lumiracoxib, etoricoxib, firocoxib, nimesulide, clonixin, licofelone, H-harpagide, flunixin, tiaprofenic acid.

Suitable examples for immunomodulatory agents (IMIDs) comprise thalidomide, lenalidomide, pomalidomide and apremilast.

Suitable examples for antiviral agents comprise ancriviroc, aplaviroc, cenicriviroc, enfuvirtide, maraviroc, vicriviroc, amantadine, rimantadine, pleconaril, idoxuridine, aciclovir, brivudine, famciclovir, penciclovir, sorivudine, valaciclovir, cidofovir, ganciclovir, valganciclovir, sofosbusvir, foscarnet, ribavirine, taribavirine, filibuvir, nesbuvir, tegobuvir, fosdevirine, favipiravir, merimepodib, asunaprevir, balapiravir, boceprevir, ciluprevir, danoprevir, daclatasvir, narlaprevir, telaprevir, simeprevir, vaniprevir, rupintrivir, fomivirsen, amenamevir, alisporivir, bevirimate, letermovir, laninamivir, oseltamivir, peramivir, zanamivir.

Suitable examples for immunostimulatory agents comprise interferons ($\alpha$-, $\beta$-, $\gamma$-, $\tau$-interferon), interleukins, CSF, PDGF, EGF, IGF, THF, levamisol, dimepranol, inosine.

Suitable examples for immunosuppressive agents comprise the group of glucocorticoids, as described before; cytostatic agents such as alkylating agents (such as cyclophosphamide), Antimetabolites such as methotrexate, azathioprine, mercaptopurine, fluorouracil, leflunomide, protein synthesis inhibitors and certain antibiotics such as dactinomycine, anthracyclines, mitomycine C, bleomycine and mithramycine, intercalating agents such as mitoxantrone; antibodies such as muromonab-CD3, rituximab, ustekinumab, alemtuzumab, natalizumab, basiliximab and daclizumab; agents acting on immunophilins such as ciclosporin, tacrolimus and sirolimus; and non-classified immunosuppressive agents such as $\beta$-interferon, $\gamma$-interferon, opioids, TNF-binding proteins such as infliximab, etanercept, adalimumab; or curcumin, catechins, mycophenolic acid, fingolimod, myriocin and fumaric acid dimethyl ester.

Suitable examples for antibiotics comprise imipenem, meropenem, ertapenem, cephalosporins, aztreonam, penicillines such as penicillin G and penicillin V, piperacillin, mezlocillin, ampicillin, amoxicillin, flucloxacillin, methicillin, oxacillin, clavulanic acid, sulbactam, tazobactam, sultamicillin, fosfomycine, teicoplanin, vancomycin, bacitracin, colistine, gramicidin, polymyxin B, tyrothricin, teixobactin, fosmidomycin, amikacin, gentamicin, kanamycin, neomycin, netilmicin, streptomycin, tobramycin, chloramphenicol, fusidinic acid, cethromycin, narbomycin, telithromycin, clindamycin, lincomycin, daptomycin, dalfopristin, quinupristin, azithromycin, clarithromycin, erythromycin, roxithromycin, linezolid, doxycycline, minocycline, tetracycline, oxytetracycline, tigecycline, norfloxacin, enoxacin, ciprofloxacin, ofloxacin, levofloxacin, moxifloxacin, metronidazole, tinidazole, aminocumarine, sulfadiazine, sulfadoxine, sulfamethoxazol, sulfasalazine, pyrimethamine, trimethoprim, and rifampicin.

Anti-infective agents is a generic term for compounds used in the treatment of bacterial, viral, fungal, protozoal and worm infections and comprises antibiotics, antiviral agents, antimycotics, antiprotozoal agents and anthelmintics.

Suitable examples for muscle relaxants comprise tercuronium, 1-ethylcarbamoyl-3-(3-trifluoromethylphenyl)pyrrolidine, metaxalone, methocarbamol, meprobamate, baclofen, carisoprodol, chlorzoxanzone, cyclobenzaprine, dantrolene, diazepam, orphenadrine, quinine, rocuronium, succinylcholine, decamethonium, pancuronium, veruronium, rapacuronium, dacuronium, duador, malouetine, dipyrandium, pipercuronium, chandonium, HS-342, atracurium, mivacurium, doxacurium, d-tubocurarine, dimethyltubocurarine, gallamine, alcuronium, anatruxonium, diadonium, fazadinium, tropeinium, cisatrucurium.

Suitable examples for antimycotics comprise abafungin, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, amorolfine, butenafine, naftifine, terbinafine, anidulafungin, caspofungin, micafungin, benzoic acid, ciclopirox, flucytosine, griseofulvin, haloprogin, tolnaftate, undecylenic acid, crystal violet, Peru balm.

Suitable examples for antiprotozoal agents comprise metronidazole, tinidazole, ornidazole, atovaquone, clioquinole, chlorquinaldole, emetine, pentamidine isethionate, eflornithine, nitrofural, halofuginone, miltefosine, chloroquine, hydroxychloroquine, mepacrine, primaquine, amodiaquine, pamaquine, piperaquine, proguanil, cyclohunail embonate, quinine, mefloquine, pyrimethamine, artmether, artemisinine, artesunate, dihydroartemisinine, halofantrine, lumefantrine, sulfadoxine.

Suitable examples for anthelmintics comprise mebendazole, praziquantel, albendazole, diethylcarbamazine, flubendazole, ivermectin, levamisole, metrifonate, niclosamide, oxyclozanide, oxamniquine, oxantel, piperazine, pyrantel, pyrantel pamoate, monopantel, derquantel, pelletierine sulfate, pyrvinium, thiabendazole, fenbendazole, triclabendazole, abamectin, suramine, emodepside, pyrvinium embonate, aminoacetonitrile.

Suitable examples for local anesthetics comprise lidocaine, lignocaine, menthol, articaine, bupivacaine, ropivacaine, benzocaine, chioroprocaine, cocaine, cyclomethycaine, dimethocaine, larocaine, piperocaine, propoxycaine, procaine, novocaine, proparacaine, tetracaine, amethocaine, cinchocaine, dibucaine, etidocaine, levobupivacaine, meplavacaine, prilocaine, trimecaine, saxitoxin, neosaxitoxin, tetrodotoxin, eugenol.

Suitable examples for analgesics comprise the NSAIDs listed above; opioid analgesics such as morphine, fentanyl, methadone, oxycodone, carfetanyl, dihydroetorphine, ohmefentanyl, etorphine, sufentanil, remifentanil, alfentanil, buprenorphine, hydromorphone, levomethadone, hydrocodone, pintramide, nalbuphine, tapentadol, pentazocine, dihydrocodeine, codeine, pethidine, tramadol, tilidine, meptazinol, naloxone, naltrexone, diprenorphine, loperamide, apomorphine; epibatidine; scopolamine; ziconitide; cannabinoids such as tetrahydrocannabinol, cannabidiol, marinol; flupirtine; ketamine and the local anesthetics listed above.

Suitable examples for anticoagulants comprise heparins, coumarins such as phenprocoumon (Marcumar) and warfarin, apixaban, rivaroxaban, edoxaban, dabigatran, ximelagatran, hirudine, lepirudine, bivalirudine, citrate, EDTA, fondaparinux, argatroban, otamixaban.

Suitable examples for thrombocyte aggregation inhibitors comprise abciximab, acetylsalicylic acid, dipyridamole, clopidogrel, eptifibatide, ilomedine, prostacyclin, prasugrel, ticagrelor, ticlopidine, tirofiban.

Tonic agents is a generic term for active agents that strengthen the body, augment the tonus or restore its physiological functions. They may be of herbal or animal origin.

Anabolic agents may support the anabolic metabolism and a strengthening of the cellular collagen scaffold. However, a wide abuse of these substances for doping in sports and bodybuilding is known. Hence, a combination with the crystalline form of luminol produced by the inventive method is only recommended insofar this is covered by the respective national legislations.

The present application refers also to a pharmaceutical composition comprising a crystalline form of luminol produced according to the method of the invention and at least one pharmaceutically acceptable excipient for prophylactic or therapeutic use in medicine.

A person skilled in the art will be familiar with the standard therapies for the aforementioned active agents. It is preferred that the respective dosage form and doses of the aforementioned active agents or combinations of active agents are oriented on already established standard therapies for the combinational active agent and/or for sodium luminolate.

In particularly preferred embodiments said pharmaceutical composition for prophylactic or therapeutic use in medicine is administered topically. In particularly preferred embodiments said pharmaceutical composition is for use in the prophylaxis or treatment of an inflammatory or autoimmune dermatologic or respiratory disease.

Most dermatologic diseases have an inflammatory background or at least show an inflammatory component among other symptoms. A comprehensive compilation of dermatologic diseases is given in ICD-10 Chapter XII. Therein dermatologic diseases are classified into the following groups: Infections of the skin; bullous disorders; dermatitis and eczema; papulosquamous disorders; urticaria and erythema; radiation-related disorders of the skin; disorders of skin appendages; other disorders of the skin.

A subgroup of inflammatory dermatologic diseases of particular interest are autoimmune dermatologic diseases. Examples for such autoimmune dermatologic diseases or diseases with an autoimmune component displaying dermatologic symptoms are, without being limiting, dermatomyositis, Behçet's disease, Behçet's disease uveitis, idiopathic thrombocytopenic purpura, psoriasis, psoriasis arthritis, vitiligo, anterior uveitis, peripheral ulcerative keratitis, bullous pemphigoid, chronic urticaria (hives), Duhring's disease (dermatitis herpetiformis), acquired bullous epidermolysis, alopecia areata, lichen sclerosus, lichen mucosae, linear IgA dermatosis, pemphigus *foliaceus*, pemphigus seborrhoicus, pemphigus vulgaris, SAPHO syndrome (synovitis, acne, pustulitis, hyperostosis, osteitis), scleroderma, Henoch-Schönlein purpura, autoimmune progesterone dermatitis, Chagas disease, acne inversa, Sharp's syndrome, Raynaud's phenomenon, pemphigus, pemphigoid, endogenous uveitis, Blau syndrome, chronic infantile neurologic cutaneous and articular syndrome, familial cold urticaria, familial Mediterranean fever, hyper-IgD syndrome, Majeed syndrome, Muckle-Wells syndrome, TNF receptor associated periodic syndrome, and atopic dermatitis.

Preferred dosage forms according to the invention are retard formulations, i.e. formulations with a delayed release of the at least one active agent. They are also known as sustained release (SR), extended release (ER, XR) or controlled/continuous release (CR) forms. Suitable formulations and carriers are known to a person skilled in the art (Kleinsorge (1995) Retardformulierungen in der medikamentösen Therapie. Leipzig, Barth 8th ed.). Most commonly, the active agent is embedded in a matrix of insoluble substances like acrylics or chitin. Thus the active agent must find its way out through orifices in the matrix. In some formulations, there is a laser-drilled hole on one side and opposite to it a porous membrane. The gastric fluid attacks this porous membrane, flows in and pushes the active agent through the drilled hole on the opposite side. In other formulations, the active agent dissolves inside the matrix swelling thereupon and forming a gel. Then the active agent is released through the pores of the gel. Other examples include specifically coated tablets resistant to gastric fluid, retard capsules containing retard pellets of the active agent that are going to be released after the dissolution of the capsule casing, multiple unit pellet systems (MUPS), oral osmotic systems, resonates, coacervation and micro-encapsulation.

With the use of such a retard formulation the release site of a drug and its pharmacokinetics can be controlled. For example, it is often desirable that a dosage form of an active agent is not dissolved before reaching a certain point of the intestines. As the pH changes along the way through the intestines, the dissolution process may be engineered to be pH-dependent. In therapeutic applications in which the absorption of an active agent through the intestinal mucosa shall be facilitated in order to augment its bioavailability it may be preferable not to use a salt of an active agent but its neutral form.

Therefore, the present application refers also to a pharmaceutical composition containing a crystalline form of luminol produced by the method according to the invention, wherein the crystalline form of luminol is formulated as a retard drug.

Yet another preferred embodiment is the formulation of luminol as an aerosol (aerosol spray). An aerosol is defined as a colloid of fine solid particles or liquid droplets in air or another gas. These particles use to have a diameter of less than 1 µm. In medicine, they have become increasingly popular for the inhalative administration of an active agent in the treatment of a respiratory disease or of the respiratory symptoms of a general disease. Aerosol particles with an effective diameter smaller than 10 µm are able to enter the bronchi, while those with an effective diameter smaller than 2.5 µm can even reach as far as the gas exchange region in the lungs. Thus, diameter size can be engineered according to the disease to be treated, as some aerosols may have unwanted side effects that may even be hazardous. Aerosols are usually administered to the patient by means of a nebulizer, a metered-dose inhaler (MDI) or a dry powder inhaler (DPI). Nebulizers use oxygen, compressed air or ultrasonic power to produce aerosol droplets from a medical solution or suspension and direct them to a mouthpiece used by the patient for inhalation. An MDI delivers a specific amount of an active agent to the lungs in form of a short burst of an aerosol. They use a propellant such as chlorofluorocarbons CFC-11, CFC-12 and CFC-14, or HFA (hydrofluoroalkanes). Penetration and bioavailability of these aerosol-born active agents can be increased by the use of phospholipids. They reduce the surface tension at the air-water interface within the alveoli, thereby reducing the pressure needed to expand the lungs. A DPI delivers the active agent to the lungs in a form of a dry powder.

Therefore, they are particularly useful for the administration of solid aerosols of an active agent, e.g. if the active agent is poorly soluble in water, or if there are stability problems with an aqueous solution. Herein, the active agent is enclosed in a capsule that has to be introduced into the DPI, or in a proprietary form inside the DPI. The patient puts the mouthpiece into his mouth and takes a sharp deep inhalation for 5-10 seconds.

Respiratory diseases with an inflammatory or autoimmune component that can be treated with aerosols include cystic fibrosis; asthma; COPD (chronic obstructive pulmonary disease); emphysema; upper respiratory tract infections such as common cold, sinusitis, tonsillitis, otitis media, pharyngitis and laryngitis; lower respiratory tract infections such as pneumonia and tuberculosis; pleural cavity diseases such as pleural mesothelioma, pleural infections, pulmonary embolus and tuberculosis; pulmonary vascular diseases such as pulmonary arterial hypertension as a sequela of COPD, pulmonary edema, granulomatosis with polyangiitis and Goodpasture's syndrome; restrictive lung diseases such as pneumoconiosis, radiation fibrosis, drug-induced airway restrictions, a sequela of rheumatoid arthritis, acute respiratory distress syndrome, infant respiratory distress syndrome, tuberculosis, idiopathic pulmonary fibrosis, idiopathic interstitial pneumonia, sarcoidosis; eosinophilic pneumonia, lymphangioleiomyomatosis, pulmonary Langerhans' cell histiocytosis, pulmonary alveolar proteinosis and interstitial lung diseases. Also when malignant tumors of the lung include an inflammatory component.

As the active agent is directly absorbed through the alveoli it is often preferred to use a neutral form instead of a salt. Thus, the present application refers also to a pharmaceutical composition containing a crystalline form of luminol produced by the method according to the invention, wherein said luminol is formulated as an aerosol for inhalative administration.

Most preferred is the administration according to the invention by means of a DPI. Also for forensic purposes, luminol can be sprayed to the site of interest in form of an aerosol.

EXAMPLES

All standard chemicals were purchased from Sigma-Aldrich.

Example 1: PXRD Analysis of Commercially Available Luminol 1 g of commercially available luminol (Merck) were analyzed by means of PXRD. Measurements were performed in transmission geometry using a STOE STADI P diffractometer with $CuK_{\alpha1}$ radiation equipped with a fast, high resolution silicon strip detector (DECTRIS Mythen1K). The samples were prepared in glass capillaries (diameter 0.5 mm). Instrumental parameters for Rietveld refinements were determined applying a Si standard. (n=3)

Crystal structure determination: TOPAS Academic (A. A. Coelho, TOPAS-Academic, version 5.0, Coelho Software, Brisbane, Australia, 2007) was used for indexing, determination of the Laue group, structure solution, and Rietveld refinement.

Structure solution was accomplished by a simulated annealing method in TOPAS Academic applying a rigid body model of a luminol molecule of the amide-hydroxy-imine tautomeric form. The molecular structure of the rigid body was obtained by DFT geometry optimization with the DMol3 module applying the generalized-gradient approximation (GGA) with the Perdew-Burke-Ernzerhof (PBE) functional as implemented in the Materials Studio software.

For structure solution six parameters were globally optimized in the simulated annealing run: Three positional and three angular parameters for the luminol.

Rietveld refinements of the resulting structure models were performed using a fundamental parameters approach for describing the peak profiles. A conjoint isotropic temperature factor for all heteroatoms was refined. Temperature factors for hydrogens were fixed to Uiso=1.27 A2.

Experiments with luminol purchased from Applichem yielded qualitatively the same results.

Example 2: Crystallization Method of Luminol

To obtain a phase-pure powder luminol (1 g, Merck) was dissolved in 80 mL of a refluxing (80° C.) ethanol-water mixture (3:1, vol %:vol %). After complete dissolution the mixture was allowed to cool slowly to room temperature within a period of 2 h. The microcrystalline powder was recovered by suction filtering and was allowed to dry at room atmosphere for 12 h.

The resulting powder was analyzed by means of PXRD, as described in Ex. 1. Also the crystal structure determination and Rietveld refinements were performed as in Ex. 1. (n=3)

Figure 5:
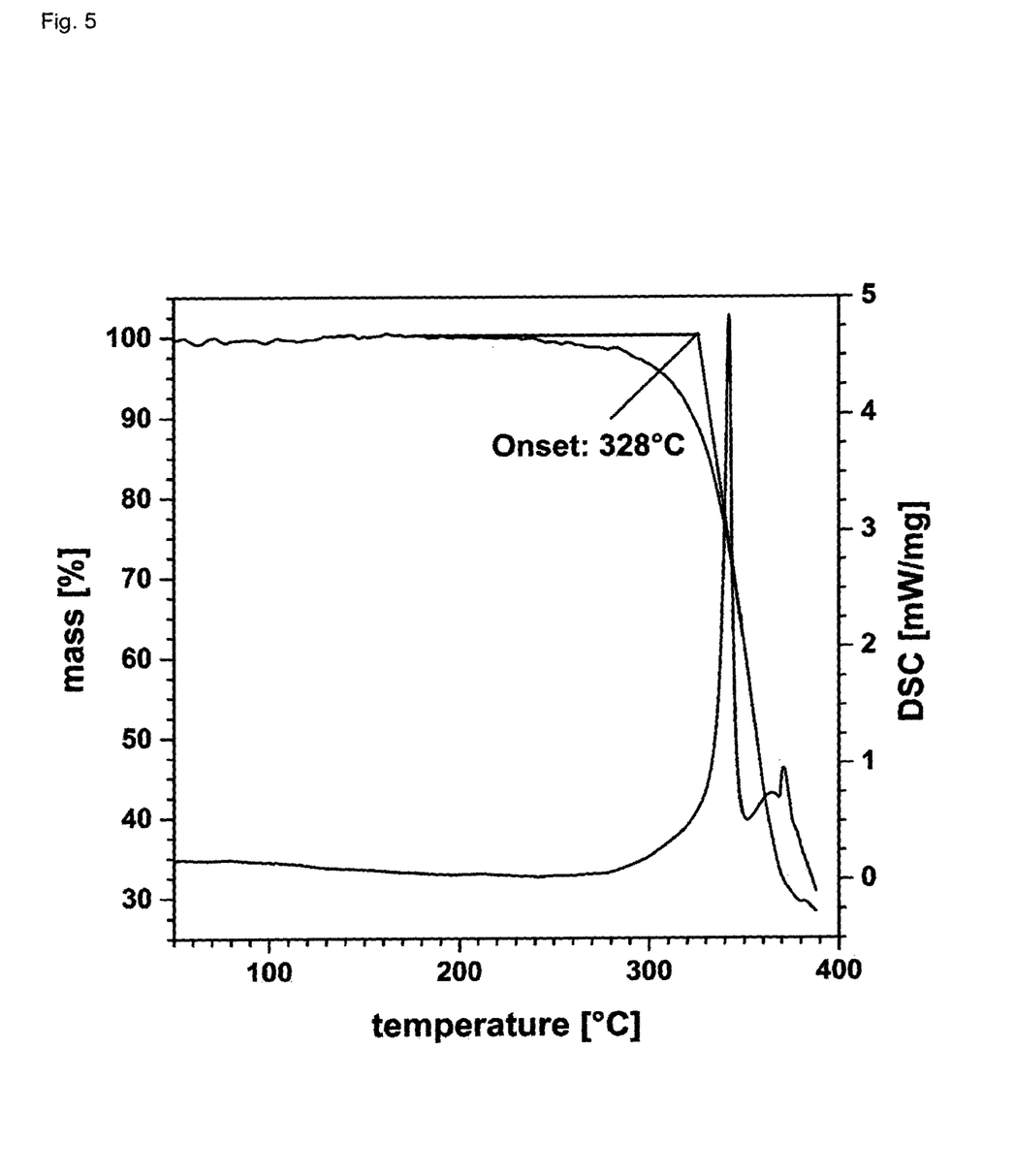
FIG. 5: TG-DSC diagram of crystalline form of 5-amino-2,3-dihydro-1,4-phthalazinedione produced by the method according to the invention. Upper trace: Mass loss determined by TG. Lower trace: Heat flow determined by DSC

Example 3: Thermal Stability of the Crystalline Form Produced by the Method According to the Invention Simultaneous thermogravimetry (TG) and differential scanning calorimetry (DSC) prove the thermal stability of the crystalline form of luminol produced by the method according to the invention up to 328±1° C. Furthermore, no solid state transformation to other forms is observed until thermal degradation of the crystalline compound sets in (FIG. 5).

ABBREVIATIONS

COPD chronic obstructive pulmonary disease
D (or: d) interplanar distance
DFT discrete Fourier transform
DPI dry powder inhaler
DSC differential scanning calorimetry
ECL electrogenerated chemiluminescence of luminol
EDTA ethylenediaminetetraacetic acid
GMP Good Manufacturing Practice
I/Io (rel) relative intensities
I/Io (%) relative intensities in percent
ICD-10 10th revision of the International Statistical Classification of Diseases and Related Health Problems
IMIDs immunomodulatory agents
mbar millibar
MDI metered-dose inhaler
min minutes
NSAIDs non-steroidal anti-inflammatory drugs
PEG polyethylene glycol
PXRD powder X-ray diffraction
SDS-PAGE sodium dodecyl sulfate polyacrylamide gel electrophoresis
TG thermogravimetry
Uiso isotropic atomic displacement parameters
v/v volume concentration
θ Bragg angle theta
% by weight percentage by weight

The invention claimed is:

1. A method for producing a crystalline form of 5-amino-2,3-dihydrophthalazine-1,4-dione comprising the following steps:
   a) Dissolving 5-amino-2,3-dihydrophthalazine-1,4-dione in a refluxing ethanol-water solution having a range from 5:1 to 1:1 (v/v) at 50 to 100° C.,
   b) cooling the solution of step a) to room temperature over a period of 60 to 240 min to afford a precipitated crystalline product,
   c) separating the precipitated crystalline product provided in step b),
   d) drying the precipitated crystalline product provided in step c) at room temperature over a period of 6 to 48 hours, and
   e) optionally, resuspending the precipitated crystalline product provided in step d) one to three times in ethanol, stirring, rewashing with ethanol and drying again, the resulting crystalline form being characterized by the following crystallography values determined by means of powder X-ray diffraction:
   D values: 11.4; 11.2; 6.9; 6.8; 6.4; 5.6; 3.6; 3.5; 3.5; 3.3; 3.2 and
   2-theta values: 7.8; 7.9; 12.8; 13.0; 13.9; 15.7; 24.9; 25.7; 25.7; 27.2; 27.5.

2. The method according to claim 1, wherein the resulting crystalline form has a crystal water content ≤0.4%.

3. The method according to claim 1, wherein the ethanol of step e) has a degree of purity ≥98%.

4. The method according claim 1, wherein the method comprises the following steps:
  a) Dissolving 5-amino-2,3-dihydrophthalazine-1,4-dione in a refluxing ethanol-water solution (3:1, v/v) at 80° C.
  b) cooling the solution of step a) to room temperature over a period of 120 min to afford a precipitated crystalline product,
  c) separating the precipitated crystalline product provided in step b), and
  d) drying the precipitated crystalline product provided in step c at room temperature for 12 hours.

* * * * *